US008663461B2

(12) United States Patent
Lee et al.

(10) Patent No.: US 8,663,461 B2
(45) Date of Patent: *Mar. 4, 2014

(54) EXTRACTION PROCESS WITH NOVEL SOLVENT REGENERATION METHODS

(71) Applicants: AMT International, Inc., Plano, TX (US); CPC Corporation, Taiwan, Taipei (TW)

(72) Inventors: Fu-Ming Lee, Katy, TX (US); Tzong-Bin Lin, Chia-Yi (TW); Kuang-Yeu Wu, Plano, TX (US); Jyh-Haur Hwang, Chia-Yi (TW); Tsung-Min Chiu, Chia-Yi (TW); Jeng-Cheng Lee, Chia-Yi (TW); Han-Tjen Jan, Chia-Yi (TW); Yuan-Fu Sun, Chia-Yi (TW)

(73) Assignees: AMT International, Inc., Plano, TX (US); CPC Corporation, Taiwan, Taipei (TW)

(*) Notice: Subject to any disclaimer, the term of this patent is extended or adjusted under 35 U.S.C. 154(b) by 0 days.

This patent is subject to a terminal disclaimer.

(21) Appl. No.: 13/783,358

(22) Filed: Mar. 3, 2013

(65) Prior Publication Data

US 2013/0228448 A1 Sep. 5, 2013

Related U.S. Application Data

(60) Provisional application No. 61/606,829, filed on Mar. 5, 2012.

(51) Int. Cl.
*C07C 7/08* (2006.01)
*C07C 7/10* (2006.01)
*B01D 3/40* (2006.01)
*C10G 21/12* (2006.01)
*C10G 21/20* (2006.01)

(52) U.S. Cl.
USPC ........... 208/321; 203/14; 203/53; 203/55; 203/58; 203/64; 208/313; 208/325; 208/330; 585/807; 585/810; 585/833; 585/857; 585/860; 585/865; 585/867; 585/901

(58) Field of Classification Search
USPC ........... 203/14, 42, 53, 55, 58, 64, 98, 99, 203/DIG. 19; 208/313, 321, 325, 330; 585/804, 807, 810, 833, 857, 860, 865, 585/867, 901
See application file for complete search history.

(56) References Cited

U.S. PATENT DOCUMENTS 3,344,202 A * 9/1967 Ziegenhain ............ 585/835
4,018,657 A * 4/1977 Sweeney et al. ........ 203/38
(Continued)

OTHER PUBLICATIONS

International application No. PCT/US2013/028783, International Search Report Date of Mailing: Jun. 26, 2013.

*Primary Examiner* — Virginia Manoharan
(74) *Attorney, Agent, or Firm* — Cascio & Zervas

(57) ABSTRACT

Solvent regeneration to recover a polar hydrocarbon (HC) selective solvent substantially free of hydrocarbons (HCs) and other impurities from a solvent-rich stream containing selective solvent, heavy HCs, and polymeric materials (PMs) generated from reactions among thermally decomposed or oxidized solvent, heavy HCs, and additives is provided. A combination of displacement agent and associated co-displacement agent squeezes out the heavy HCs and PMs from the extractive solvent within a solvent clean-up zone. Simultaneously, a filter equipped with a magnetic field is positioned in a lean solvent circulation line to remove paramagnetic contaminants. The presence of the co-displacement agent significantly enhances the capability of the displacement agent in removing the heavy HCs and PMs from the extractive solvent. As a result, the solvent regeneration system operates under milder conditions and minimizes or eliminates the need for including a high temperature, energy intensive and difficult-to-operate thermal solvent regenerator.

25 Claims, 4 Drawing Sheets

(56) References Cited

U.S. PATENT DOCUMENTS

| | | |
|---|---|---|
| 7,666,299 B2 | 2/2010 | Wu et al. |
| 7,871,514 B2 | 1/2011 | Lee et al. |
| 7,879,225 B2 * | 2/2011 | Lee et al. ............... 208/313 |
| 8,002,953 B2 * | 8/2011 | Lee et al. ............... 203/19 |
| 8,172,987 B2 * | 5/2012 | Lee et al. ............... 203/19 |
| 8,246,815 B2 | 8/2012 | Wu et al. |
| 8,471,088 B2 * | 6/2013 | Monson et al. ............... 585/833 |
| 2007/0000809 A1 | 1/2007 | Lin et al. |
| 2009/0038991 A1 | 2/2009 | Wu et al. |
| 2009/0105514 A1 | 4/2009 | Lee et al. |
| 2009/0255853 A1 | 10/2009 | Lee et al. |
| 2009/0272702 A1 | 11/2009 | Yen et al. |
| 2010/0065504 A1 | 3/2010 | Yen et al. |
| 2012/0037542 A1 | 2/2012 | Wu et al. |
| 2012/0165551 A1 | 6/2012 | Yen et al. |
| 2012/0197057 A1 * | 8/2012 | Monson et al. ............... 585/857 |
| 2012/0228231 A1 | 9/2012 | Yen et al. |

\* cited by examiner

EXTRACTION PROCESS WITH NOVEL SOLVENT REGENERATION METHODS

REFERENCE TO RELATED APPLICATIONS

This application claims priority to U.S. Provisional Patent Application No. 61/606,829 which was filed on Mar. 5, 2012.

FIELD OF THE INVENTION

The present invention relates generally to removing heavy hydrocarbons and polymeric sludge from a selective solvent after the solvent contacts a feed mixture containing aromatic and non-aromatic hydrocarbons and more particularly to solvent regeneration techniques whereby a co-displacement agent is used to enhance the capability of a primary displacement agent.

BACKGROUND OF THE INVENTION

In extractive distillation (ED) and liquid-liquid extraction (LLE) processes for aromatics recovery, the solvent is circulated in a closed loop indefinitely. The feedstock is typically treated in a prefractionator to remove the heavy portion before being fed into the EDC or LLE column. Nevertheless, measurable amounts of heavy hydrocarbons (HCs) pass through even a well-designed prefractionator operating under normal conditions. The level of heavy HCs in the feed stream is significantly higher for a poorly operated or malfunctioned prefractionator. To remove the heavy HCs and the polymerized heavy materials derivate from oxidized solvent, conventional commercial LLE processes use a thermal solvent regenerator where a small slip stream of the lean solvent is heated to recover the regenerated solvent and heavy components that have boiling points lower than that of the solvent. The heavy polymeric materials (PMs), that have boiling points higher than that of the solvent, are removed as sludge from the bottom of the solvent regenerator.

U.S. Pat. No. 4,048,062 to Asselin discloses a LLE process for aromatics recovery in which a portion of lean solvent from the bottom of a solvent recovery column (SRC) is introduced into a solvent regenerator (SRG). A stripping steam that is introduced into the SRG separately is recovered with the regenerated solvent and then introduced into the SRC as a portion of the total stripping steam. This solvent regeneration scheme works because, within the same type of molecules, the higher the boiling point, the lower the polarity (affinity with the extractive solvent). Consequently, a major portion of the measurable heavy ($C_9$ to $C_{12}$) HCs in the feedstock is rejected by the solvent phase in the LLE column and is removed with the raffinate phase as a part of the non-aromatic product.

In an ED process for aromatics recovery, the heavy HCs tend to remain in the rich solvent at the bottom of the extractive distillation column (EDC) due to their high boiling points. Even for a narrow boiling-range ($C_6$-$C_7$) feedstock, there can be measurable amounts of heavy ($C_9^+$) HCs that are trapped and accumulated in the solvent, which can only be removed from the solvent by increasing the severity of the SRC (higher temperature and vacuum level, and more stripping steam) and/or by increasing the loading of the SRG. Neither alternative is desirable. Moreover, for the full boiling-range ($C_6$-$C_8$) feed, the boiling points of the heavy HCs are too high to be stripped from the solvent in the SRC and, as a result, they accumulated in the solvent as the solvent is circulated between the EDC and the SRC indefinitely in a closed loop.

The solvent regeneration of the Asselin scheme is not suitable for the ED process. The scheme was designed for LLE processes to remove minor amounts of PMs generated from reactions between the oxidized or decomposed solvent components and traces of the heavy HCs in the solvent. When this scheme is applied to ED processes, heavy HCs inevitably accumulated and polymerized in the closed solvent loop until the polymerized materials reach boiling points that are higher that of sulfolane (>285° C.) before they can be removed from the bottom of the solvent regenerator. This accumulation is potentially disastrous since the presence of excessive PMs not only changes the solvent properties (selectivity and solvency) significantly but the polymers also plug process equipment to render the ED process inoperable.

U.S. Pat. No. 7,666,299 to Wu, et al. and U.S. Pat. No. 7,871,514 to Lee, et al. disclose a technique for removing heavies from solvent that is based on the observation that most of extractive solvents for ED and LLE are water soluble. In practice, a split solvent stream is introduced into a water washing zone and contacts a stream of process water, which is circulated in a closed loop. Solvent dissolves into the water phase while the heavy HCs and PMs are rejected by the water. In this fashion, the heavy HCs and PMs are removed from the solvent stream and accumulate in the HC phase. Because this water wash method requires much water, it is often difficult to achieve the proper balance and distribution of the process water in the closed system.

U.S. Pat. No. 8,246,815 to Wu, et al. describes a method of removing heavy HCs and PMs that are trapped in the closed solvent loop in an ED or LLE process for aromatic HCs recovery. Light hydrocarbons, such as non-aromatic HCs in the raffinate stream, function as "displacement agents." The light HCs "squeeze" the heavy HCs and PMs from the extractive solvent, especially when the heavy HCs in the solvent are in the $C_9^+$ molecular weight range.

SUMMARY OF THE INVENTION

The present invention is based in part on the development of techniques for using a co-displacement agent to significantly enhance the capability of a displacement agent in removing the heavy HCs and PMs from the extractive solvent. The novel methods are particularly suited for incorporation into processes wherein a feed mixture containing aromatic and non-aromatic HCs is contacted with a selective solvent in an extraction zone consisting of an extractive distillation column (EDC), liquid-liquid, extraction (LLE) column, or combination thereof. A rich solvent stream comprising the solvent and aromatic HC is generated and fed to a solvent recovery column or zone to recover the purified aromatic HCs and the lean solvent which contains solvent and measurable amounts of heavy HC's and polymeric sludge.

In one aspect, the invention is directed to a method for recovering a polar HC selective solvent substantially free of HCs and other impurities from a solvent-rich stream containing the selective solvent, measurable amounts of heavy HCs, and PMs generated from reactions among thermally decomposed or oxidized solvent, heavy HCs, and additives, which method includes the steps of:

(a) introducing a feed containing polar and less polar HCs into a middle portion of an extractive distillation column (EDC) and introducing a solvent-rich stream into an upper portion of the EDC as a selective solvent feed;

(b) recovering a water-containing, less polar HC-rich stream from a top of the EDC and withdrawing a first solvent-rich stream containing solvent and polar HCs from a bottom of the EDC;

(c) introducing the first solvent-rich stream into a middle portion of a solvent recovery column (SRC), recovering a polar HC-rich stream, that is substantially free of solvent and less polar HCs, from a top of the SRC, and removing a second solvent-rich stream from a bottom of the SRC;

(d) introducing a first portion of the second solvent-rich stream into the upper portion of the EDC in step (a) as the selective solvent feed;

(e) cooling a second portion of the second solvent-rich stream in step (c), mixing the cooled solvent-rich stream with a portion of water phase from step (h), and introducing the mixture into an upper portion of a solvent clean-up zone to form a solvent phase;

(f) introducing a light HC-rich stream into a lower portion of the solvent clean-up zone, as a heavy HC displacement agent, to squeeze out heavy HCs and PMs from the solvent phase into a HC phase;

(g) withdrawing an accumulated HC phase containing heavy HCs, PMs and minor amounts of solvent from an upper portion of the solvent clean-up zone, and recovering a solvent phase containing solvent and light HCs, which serves as heavy HC displacement agents, and has substantially reduced levels of heavy HCs and PMs, from a lower portion of the solvent clean-up zone;

(h) introducing the HC phase from the solvent clean-up zone in step (g) into a water wash zone to remove the minor amounts of solvent from the HC phase into the water phase; and (i) introducing the solvent phase from the solvent clean-up zone in step (g) into a lower portion of the EDC in step (a) as part of a selective solvent feed to recycle purified solvent into a solvent loop.

In another aspect, the invention is directed to a method for recovering a polar HC selective solvent substantially free of HCs and other impurities from a solvent-rich stream containing the selective solvent, measurable amounts of heavy HCs, and PMs generated from reactions among thermally decomposed or oxidized solvent, heavy HCs, and additives, which method includes the steps of:

(a) introducing a feed containing polar and less polar HCs into a middle portion of a LLE column and introducing a solvent-rich stream into an upper portion of the LLE as a selective solvent feed;

(b) recovering a water-containing, less polar HC-rich stream from a top of the LLE column and withdrawing the first solvent-rich stream containing solvent, polar HCs and minor amounts of less polar HCs from a bottom of the LLE;

(c) introducing a mixture comprising the first solvent-rich stream and a minor portion of a third solvent-rich stream from a bottom of a solvent recovery column (SRC), into an upper portion of an extractive stripping column (ESC), recovering a HC-rich vapor containing less polar HCs and a significant amount of benzene and heavier aromatics, which is condensed and recycled to a lower portion of LLE column as the reflux, and withdrawing a second solvent-rich stream containing solvent and polar HCs, which is substantially free of less polar HCs, from a bottom of the ESC;

(d) introducing the second solvent-rich stream in step (c) into a middle portion of the SRC, withdrawing a polar HC-rich stream, which is substantially free of solvent and non-polar HCs, from a top of the SRC, and removing a third solvent-rich stream from a bottom of the SRC;

(e) introducing a portion of the third solvent-rich stream into the upper portion of the LLE column in step (a) as the selective solvent feed;

(f) cooling a minor portion of the third solvent-rich stream in step (d), mixing the cooled solvent-rich stream with a portion of water phase from step (i), and introducing the mixture into an upper portion of a solvent clean-up zone to form a solvent phase;

(g) introducing a light HC-rich stream into a lower portion of the solvent clean-up zone, as a heavy HC displacement agent, to squeeze out heavy HCs and PMs from the solvent phase into a HC phase;

(h) withdrawing an accumulated MC phase containing heavy HCs, PMs, and minor amounts of solvent from an upper portion of the solvent clean-up zone and recovering the solvent phase containing solvent, light HCs, which serves as heavy hydrocarbon displacement agents, and having substantially reduced levels of heavy HCs and PMs, from a lower portion of the solvent clean-up zone;

(i) introducing the HC phase from the solvent clean-up zone in step (h) into a water wash zone to remove the minor amounts of solvent from the HC phase into the water phase.

(j) introducing the solvent phase from the solvent clean-up zone in step (h) into a lower portion of the ESC in step (c) as a way to recycle purified solvent into a solvent loop.

A filter enhanced with a magnetic field can be installed in the lean solvent circulation line to work simultaneously with the solvent clean-up zone to remove paramagnetic contaminants in the lean solvent to minimize the function of or eliminate the need for a high temperature, energy intensive and difficult-to-operate thermal solvent regenerator.

DETAILED DESCRIPTION OF THE INVENTION

The techniques of the present invention can be integration into an ED or LLE process for the selective separation and recovery of polar HCs from a mixture containing the polar and less polar HCs. The inventive processes will be described in relation to the separation and recovery of aromatic HCs from mixtures containing aromatics and non-aromatics, comprising paraffins, isoparaffins, naphthenes, and olefins, but it is understood that the techniques are applicable to a multitude of mixtures. Suitable extractive solvents include, for example, sulfolane, alkyl-sulfolane, N-formyl morpholine, N-methyl pyrrolidone, tetraethylene glycol, triethylene glycol, diethylene glycol, and mixtures thereof, with water as the co-solvent. For aromatic HC recovery, the preferred solvents for the ED process comprise sulfolane with water as the co-solvent and non-aqueous N-formyl morpholine; the preferred solvents for the LLE process comprise sulfolane and tetraethylene glycol and both with water as the co-solvent. The most preferred solvent for both the ED and LLE processes is sulfolane with water as the co-solvent.

Figure 1:
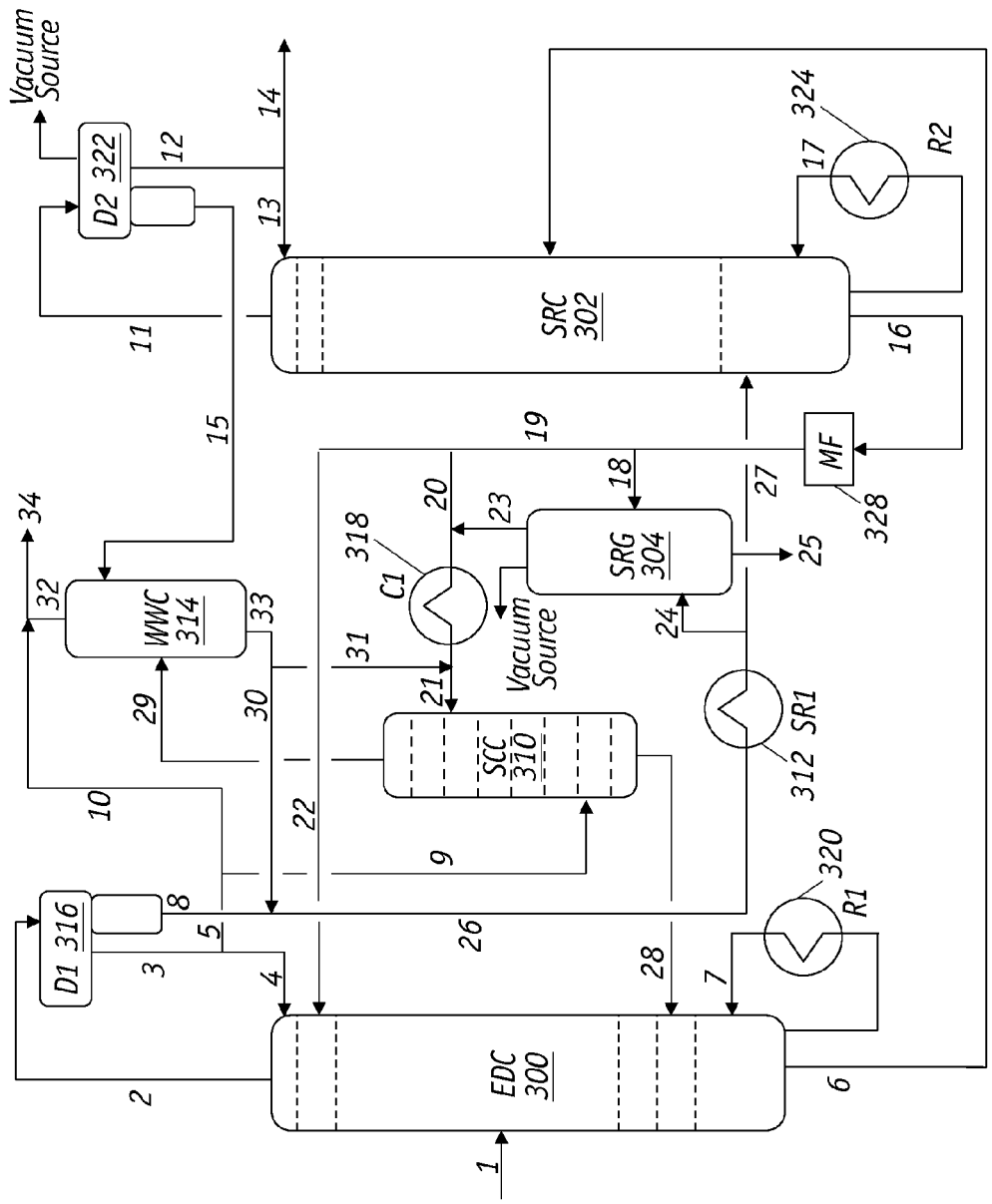
FIG. 1 illustrates an ED process with a solvent clean-up system that includes a counter-current extractor, a magnetically enhanced filter, and a thermal regenerator.
Figure 3:
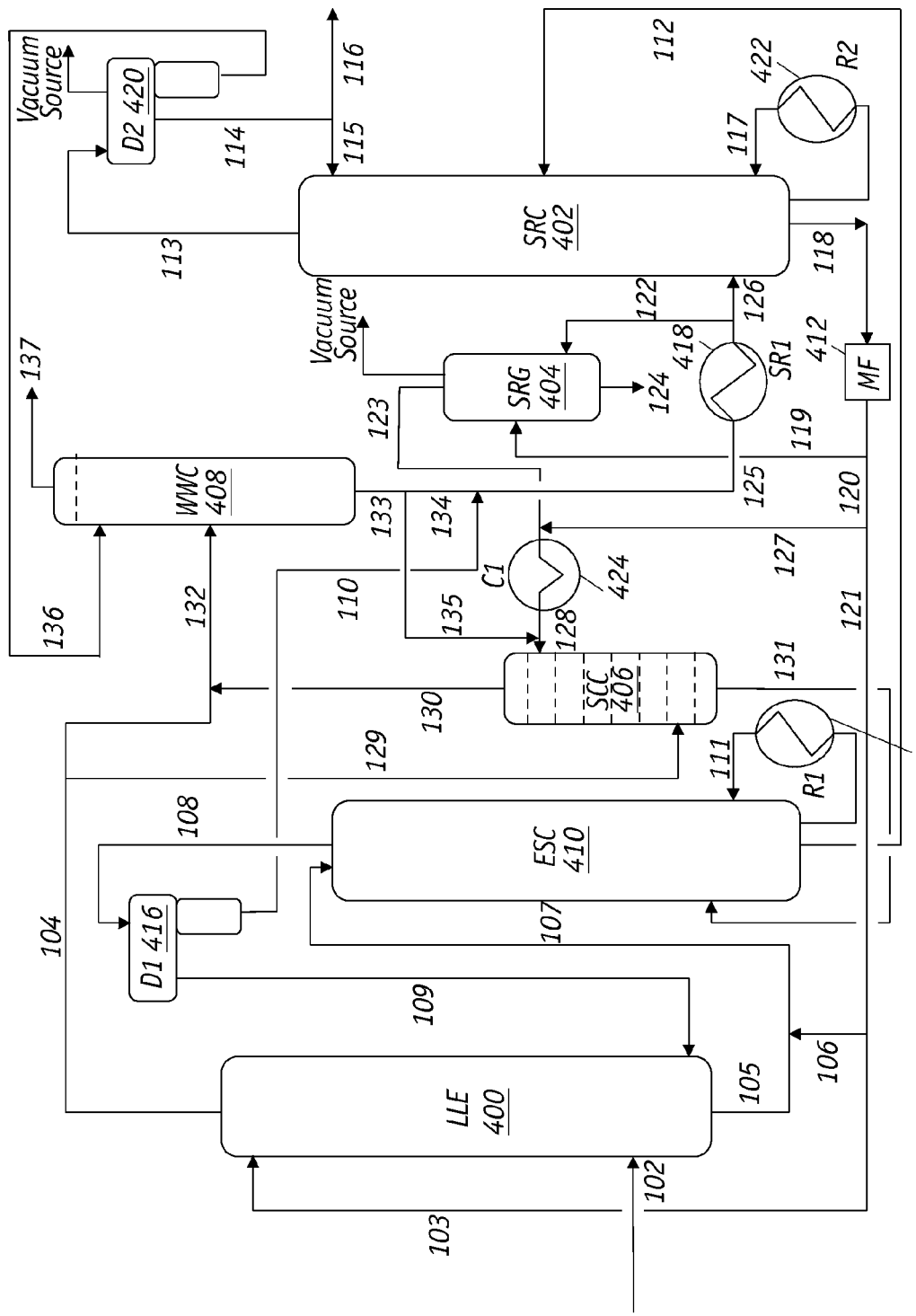
FIG. 3 illustrates a LLE process with a solvent clean-up system including a counter-current extractor, a magnetically enhanced filter, and a thermal regenerator.

In one feature of the invention for aromatic HC recovery as depicted in FIGS. 1 and 3, a portion of the lean solvent in an ED or LLE process, which contains measurable amounts of heavy HCs and PMs, is withdrawn from the bottom of a solvent recovery column (SRC) and combined with regenerated solvent from an overhead of a thermal solvent regenerator. The combined lean solvent stream, after cooling, is then mixed with a slip water-rich stream from the bottom of the water wash column (WWC) (as co-displacement) and introduced into the solvent clean-up system or zone (SCZ). The SCZ preferably consists of a column with trays, packings or rotating discs, or a pulse column, or a multi-stage mixer/settlers. A portion of the raffinate stream from the EDC overhead in the ED process (or the LLE column overhead in the LLE process), is also fed to the SCZ to contact the mixed lean solvent stream with increased water content.

Preferably, the raffinate stream, as a displacement agent, contacts the mixed solvent stream with increased water content, with the water being the co-displacement agent, in a counter-current fashion in order to squeeze out the heavy HCs and polymeric PMs from the solvent phase into the HC phase. The higher water content augments the raffinate stream in displacing the heavies from the solvent phase. The solvent phase, which contains essentially the solvent, most of the benzene and other aromatic components from the raffinate stream (the displacement agent), and much reduced levels of heavy HCs and PMs, is withdrawn continuously from the SCZ and fed into the lower portion of the EDC (or the lower portion of the extractive stripping column (ESC) of a LLE process), as a way to enhance the solvent selectivity in the single phase region in the EDC (or ESC) with increased water content (the co-displacement agent), to recycle purified solvent into the closed solvent loop, and to recover the aromatic HCs, especially benzene, which is lost to the raffinate stream. A HC phase from the SCZ, containing the "squeezed" heavy HC's and PMs as well as most of non-aromatic components in the raffinate stream, is removed continuously from the SCZ and fed to a WWC to remove any solvent in the HC phase. The SCZ is operated such that the benzene content of its HC phase after combining with the raffinate stream from the EDC (or LEE column), before or after the WWC, is controlled at a desirable level. For example, if the combined HC stream is used for gasoline blending, its benzene concentration should be below one volume percent.

Alternatively, any desulfinized light HC mixture can be used to replace the EDC or LLE column raffinate stream as the displacement agent to remove the heavy HCs and PMs from the lean solvent. With the present invention, the incorporation of a SCZ to remove a substantial portion of the heavy HCs and PMs will greatly reduce the loading requirements of the thermal solvent regenerator, when the latter is employed, and renders the process easier to operate, especially for the ED process.

A filter, preferably one that is enhanced with a magnetic field, can be installed in the solvent loop to selectively remove the paramagnetic contaminants generated from the interaction among decomposed solvent, various solvent additives and the heavy HCs with iron sulfides and iron oxides. Suitable filters with magnets are described in U.S. Pat. Publication Nos. 20090272702, 20100065504, 20120165551, and 20120228231, which are incorporated herein by reference.

Figure 2:
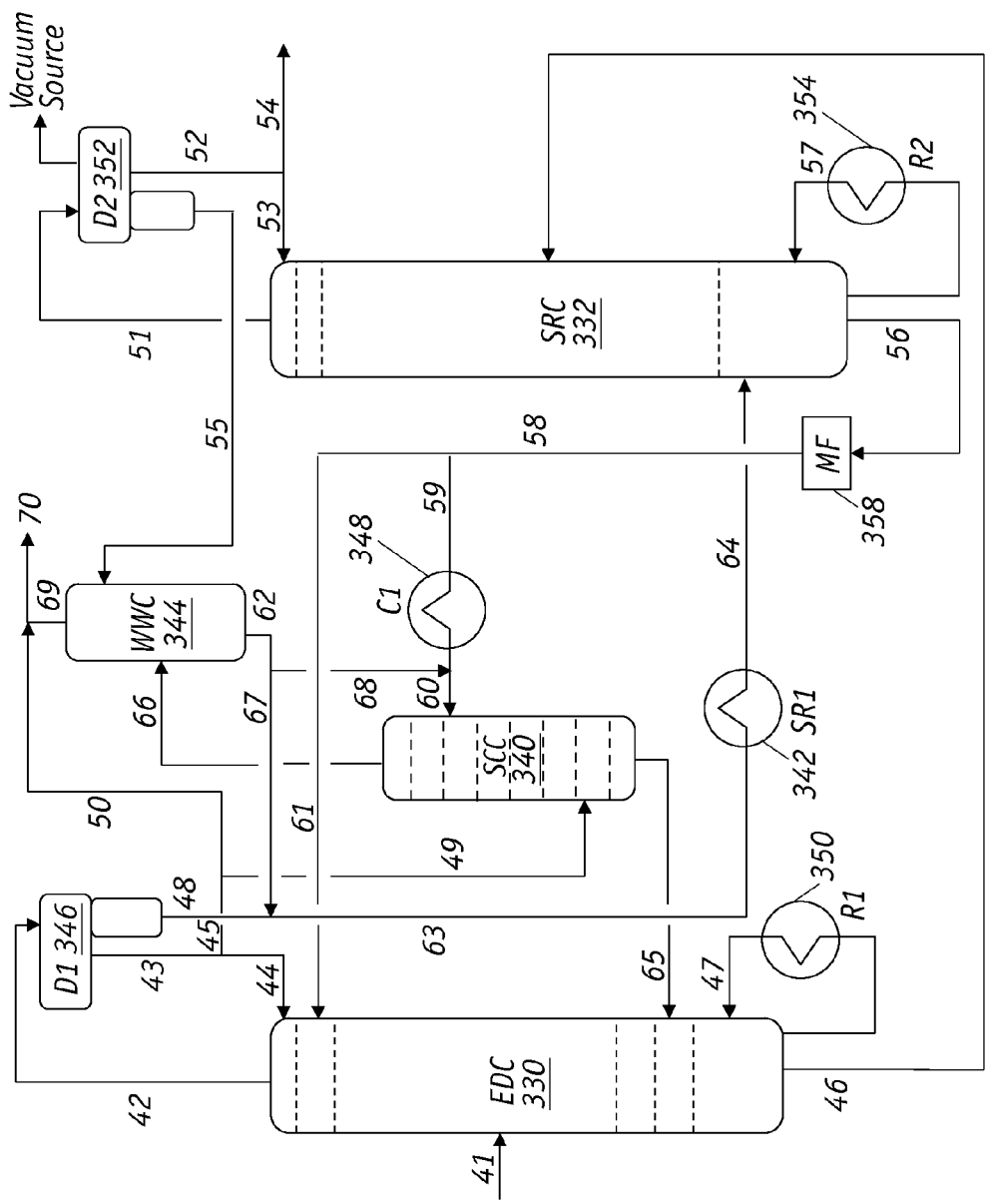
FIG. 2 illustrates an ED process with a solvent clean-up system that includes a counter-current extractor and a magnetically enhanced filter.
Figure 4:
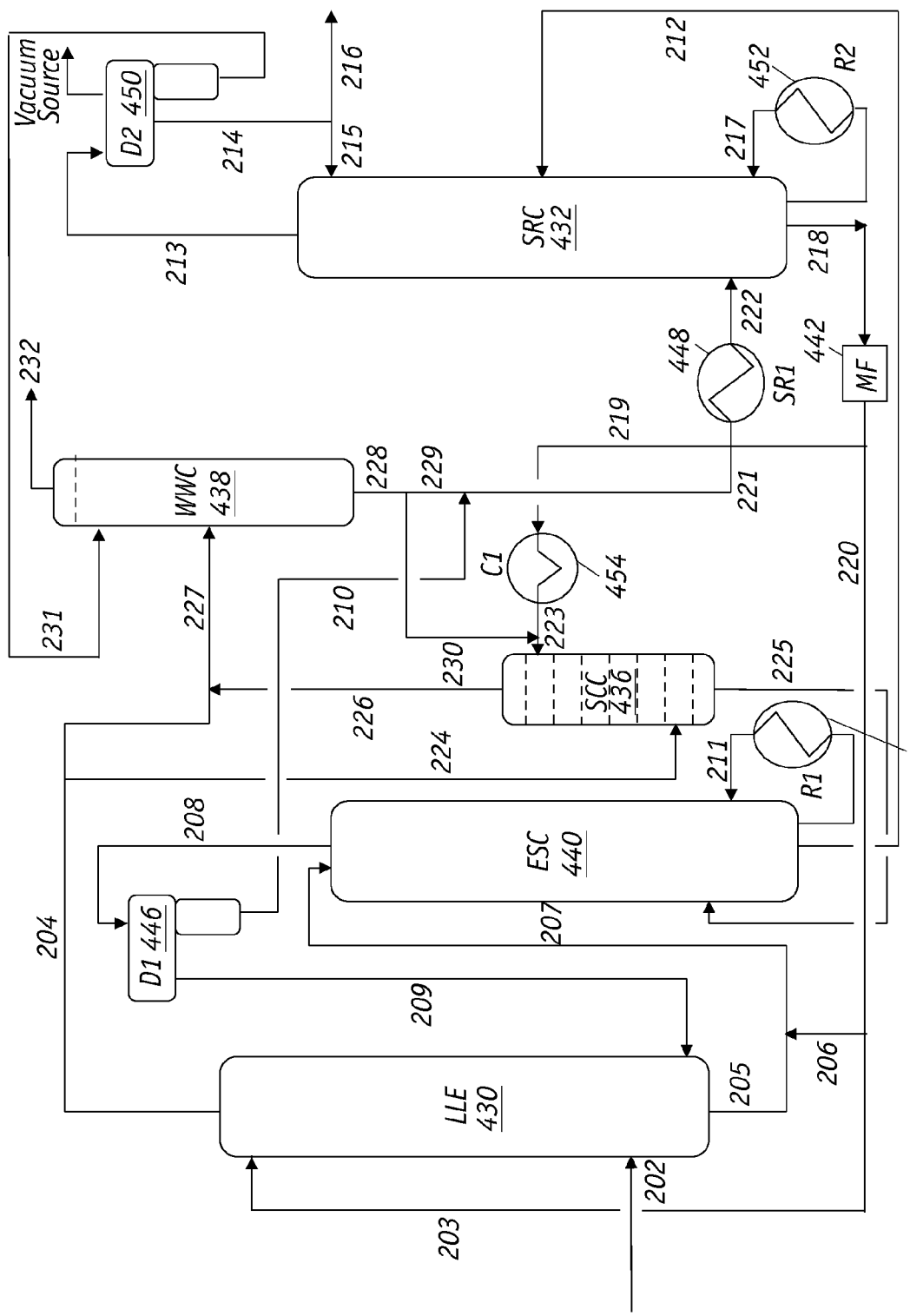
FIG. 4 illustrates a LLE process with a solvent clean-up system including a counter-current extractor and a magnetically enhanced filter.

In another feature of the invention as depicted in FIGS. 2 and 4, a solvent regeneration scheme employs an efficient, low temperature and energy-saving solvent clean-up zone or system. The process does not require any high temperature and energy-intensive thermal solvent regenerator. A portion of a lean solvent stream that is withdrawn from the bottom of a SRC is diverted and, after cooling, combined with a water-rich slip stream from the bottom of the WWC (as a co-displacement agent), before introducing into a SCZ. A portion of raffinate stream from the overhead of the EDC in the ED process (or the LLE column in the LLE process) is also fed to the SCZ as a displacement agent, to contact said diverted lean solvent stream with increased water content.

The solvent clean-up operation is typically conducted in a continuous multi-stage contacting device, and preferably in one that is designed for counter-current extraction. Suitable designs includes columns with trays, packings, or rotating discs, pulse columns, any other rotating type contactors, and multi-stage mixers/settlers. The solvent phase containing essentially the solvent, increased amount of water, most of aromatic components from the raffinate stream (the displacement agent), especially benzene, and much reduced levels of heavy HCs, is withdrawn continuously from the SCZ and fed to the lower portion of the EDC or ESC, as a way to enhance the solvent selectivity in the single phase region of the EDC (or the ESC), to recycle purified solvent into the closed solvent loop, and to recover the aromatic HCs, especially benzene, which is lost to the raffinate stream. The HC phase containing the "squeezed" heavy HCs and PMs is removed periodically from the SCZ. The SCZ is operated such that the benzene content of its HC phase after combining with the raffinate stream from the EDC (or LLE column), before or after the WWC, is controlled at a desirable level.

Alternatively, any desulfurized light HC mixture can be used to replace the raffinate stream as the displacement agent remove heavy HCs and PMs from the lean solvent and to recover the aromatics from the raffinate stream, especially benzene. Again, a filter that is enhanced with a magnetic field can be installed in the solvent loop to selectively remove the paramagnetic contaminants from the lean solvent stream.

In the above-described embodiments, since the $C_9^+$ heavy HCs are recovered from the lean solvent in the SCZ, the EDC in the ED process is preferably operated under further relaxed conditions by releasing the maximum allowable benzene to the overhead raffinate stream and by keeping substantially all $C_9^+$ HCs in the bottom of the EDC with the rich solvent (extract) stream. The SRC is preferably operated under such conditions as to strip only $C_8$ and lighter HCs from the rich solvent stream and to keep substantially all $C_9$ and heavier HCs in the bottom of the SRC with the lean solvent stream.

FIG. 1 depicts an ED process for aromatic HCs recovery which employs an extractive distillation column (EDC) 300, solvent recovery column (SRC) 302, thermal solvent regenerator (SRG) 304, solvent clean-up column (SCC) 310, and water washing column (WCC) 314. A HC feed containing aromatic and non-aromatic HCs is fed via line 1 to the middle portion of EDC 300, while a lean solvent from the bottom of SRC 302 is fed via lines 16, 19, and 22 to near the top of EDC 300 below the overhead reflux entry point for line 4.

Non-aromatics vapor exiting the top of EDC 300 through line 2 is condensed in a condenser (not shown) and the condensate is transferred to an overhead receiver D1 316, which serves to effect a phase separation between the non-aromatic HCs and the water phases. A portion of the non-aromatic HC phase is recycled to the top of EDC 300 as reflux via lines 3 and 4 and a second portion is withdrawn as the raffinate stream through line 5.

A part of the raffinate stream in line 5 is withdrawn as a raffinate product through lines 10 and 34. A rich solvent consisting of solvent, aromatics free of non-aromatics, and measurable amounts of heavy HCs and PMs is withdrawn from the bottom of EDC 300 and transferred to the middle portion of SRC 302 via line 6. Stripping steam is injected from steam generator SR1 312 via line 27 into the lower portion of SRC 302 to assist in removing the aromatic HCs from the solvent. A portion of the rich solvent heated in reboiler R1 320 and recycled to the bottom of EDC 300 via line 7. An aromatic concentrate, containing water and being substantially free of solvent and non-aromatic HCs, is withdrawn as an overhead vapor stream from SRC 302 and introduced into an overhead receiver D2 322 via line 11 after being condensed in a cooler (not shown). In order to minimize the bottom temperature of SRC 302, receiver D2 322 is connected to a vacuum source to generate sub-atmospheric conditions in SRC 302.

Overhead receiver D2 322 serves to effect a phase separation between the aromatic HCs and the water phases. A portion of the aromatic HC phase in line 12 is recycled to the top of SRC 302 as reflux via line 13, while the remaining portion is withdrawn as aromatic HC product through line 14. The water phase that accumulates in the water leg of overhead receiver D2 322 is fed via line 15 to WWC 314 as wash water at a location below the interface between the HC phase and the water phase near the top of WWC 314. Solvent is removed from the HC phase from SCC 310 through a counter-current water wash and the solvent-free non-aromatics, which accumulate in the phase, are then withdrawn from the top of WWC 314 as solvent-free non-aromatic products through line 32. A water phase, containing the solvent, exits through lines 33, 30 from the bottom of WWC 314 and is combined with line 8, which is the water phase from overhead receiver D1 316, and is fed to SR1 312 via line 26 where it is transformed into stripping steam that is introduced into SRC 302 via line 27 and into SRG 304 via line 24.

A greater proportion of the lean solvent from the bottom of SRC 302 is recycled through a magnetic enhanced filter MF 328 via lines 16, 19, and 22 and is supplied to the upper portion of EDC 300 for extracting the aromatic HCs. A split stream of the lean solvent from the SRC bottom is diverted into SRG 304 via line 18 and steam is introduced into SRG 304 through line 24, at a location below the lean solvent feed entry point. A portion of the lean solvent is heated in reboiler R2 324 and recycled to the bottom of SRC 302 via line 17. Deteriorated solvent and polymeric sludge are removed as a bottom stream through line 25, while the regenerated solvent and substantially all the stripping steam, are recovered as an overhead stream 23. This vapor in line 23 and a split lean solvent from the bottom of SRC 302 in line 20 are combined to form the mixture in line 21, which contains the solvent, measurable amounts of heavy HCs and substantially all the stripping steam from SRG 304. After cooling and condensing in the cooler C1 318, a slip water-rich stream from the bottom of WWC 314 is added to the stream in line 21 to provide a controlled amount of water via line 31 to the lean solvent stream as a co-displacement agent, which is then introduced into the upper portion of SCC 310 below the location of solvent/HC interface.

A portion of the raffinate stream from EDC 300 is fed to the lower portion of SCC 310 via line 9 as the displacement agent to contact the solvent phase counter-currently to squeeze out the heavy HCs and PMs from the solvent phase into the HC phase in SCC 310. Alternatively, any external desulfurized light HC stream can be used effectively as the displacement agent. A solvent phase containing essentially purified solvent, most of the aromatics components from the raffinate stream (the displacement agent), and substantially reduced levels of heavy HCs and PMs is continuously withdrawn from the bottom of SCC 310 and introduced through line 28 into the lower portion of EDC 300, as a way of recycling the purified solvent into the solvent loop, to recover the aromatic HCs, especially benzene, which is lost to the raffinate stream, and to enhance the solvent selectivity in the single phase region of EDC 300 due to increased water content (the co-displacement agent) in the recycled solvent phase from SCC 310.

The HC phase accumulates continuously at the top of SCC 310 and is removed periodically from the overhead of SCC 310 and fed to WWC 314 via lines 29 under interface level control. The solvent clean-up operation can also be achieved by employing other contacting devices. Preferred apparatuses include continuous multi-stage contacting devices configured for counter-current extraction, such as multi-stage mixers/settlers or rotating type contactors.

In an application of the ED process using sulfolane as the solvent, EDC 300 is operated at a reduced solvent-to-HC feed weight ratio of 2.0 to 4.0, preferably 1.5 to 3.0, depending upon the boiling range of the HC feedstock, to allow 1 to 10 wt %, preferably 2 to 5 wt % benzene in the raffinate stream from the EDC overhead. The temperature of the overhead vapor from SRG 304 typically ranges from 150° to 200° C., and preferably from 160° to 180° C. under a pressure of 0.1 to 10 atmospheres, and preferably of 0.1 to 0.8 atm. The mixture comprising of solvent vapor from SRG 304 and lean solvent from SRC 302 is condensed and cooled in cooler C1 318 to a temperature in the range of approximately 0 to 100° C., and preferably of 25 to 80° C. The temperature of the raffinate stream from EDC 300, which is fed to SCC 310 as the displacement agent, ranges from 0 to 100° C., preferably from 25 to 50° C. The raffinate feed-to-lean solvent feed weight ratio in SCC 310 is typically from 0.1 to 100, and preferably from 0.1 to 10. The contacting temperature in SCC 310 typically ranges from 0° to 100° C., and preferably from 25 to 80° C. The operating pressure of SCC 310 typically ranges from 1 to 100 atm., and preferably from 1 to 10 atm. The weight ratio between the cooled solvent-rich stream mixture in line 21 and the water-rich stream in line 31 is in the range of 200:1 to 10:1, preferably in the range of 100:1 to 20:1; the desired ratio is achieved by adjusting the flow rate of the water-rich stream in line 31. The solvent phase from SCC 310, containing essentially all the solvent, the added amount of water, most of aromatic components from the raffinate stream (the displacement agent), especially benzene, and much reduced levels of heavy HCs and polymeric materials, is fed to the lower portion of EDC 300 to enhance the solvent selectivity in the single liquid phase region due to added water in the solvent phase.

The operation conditions of the SCZ are preferably selected to achieve the following three main objectives: (1) The benzene content in the HC phase is at such a level that the benzene concentration in the raffinate stream through combination of lines 10 and 32 meets product specifications. For example, the benzene concentration in the raffinate stream in line 34 should below one volume percent for gasoline blending. (2) The content of heavy HCs and PMs in the solvent phase withdrawn in line 28 is kept at a desirable range to maintain the solvent performance. (3) The water content in the lean solvent feed to the SCZ is controlled by adjusting water addition in order to maximize the heavy HCs removal from the solvent phase and minimize benzene loss to the HC phase (raffinate product after water wash).

FIG. 2 illustrates an ED process for aromatic HCs recovery in which SCC 340 uses the EDC raffinate, as the displacement agent, and the added water to the lean solvent, which functions the co-displacement agent, are employed to regenerate the solvent. The conventional high temperature and energy intensive thermal solvent regenerator is not required in this solvent regeneration scheme. This ED process employs extractive distillation column (EDC) 330, solvent recovery column (SRC) 332, a solvent clean-up column (SCC) 340, water washing column (WWC) 344, and inline magnetic filter (MF) 358.

A HC feed containing a mixture of aromatic and non-aromatic HCs is fed via line 41 to the middle portion of EDC 330, while lean solvent from the bottom of SRC 332 is fed via lines 56, 58, and 61 to near the top of EDC 330 below the overhead reflux entry point for line 44. The lean solvent from SRC 332 can be filtered with a magnet-enhanced filter MF 358 that removes iron rust particulates and other polymeric sludge that are paramagnetic in nature. Non-aromatics vapor exiting the top of EDC 330 through line 42 is condensed in a condenser (not shown) and the condensate is transferred to an overhead receiver D1 346, which serves to effect a phase separation between the non-aromatic HCs and the water phases. A portion of the non-aromatic HC phase in line 43 is recycled to the top of EDC 330 as reflux via line 44 while a second portion is withdrawn as through line 45. A part of the raffinate stream in line 45 is withdrawn as the raffinate product through lines 50 and 70.

A rich solvent consisting of the solvent, purified aromatics and measurable amounts of heavy HCs and PMs is withdrawn from the bottom of EDC 330 and transferred to the middle portion of SRC 332 via line 46. Rich solvent is also heated in reboiler R1 350 and recycled to the bottom of EDC 330 via line 47. Stripping steam is injected from steam generator SR1 342 via line 64 into the lower portion of SRC 332 to assist in the removal of aromatic HCs from the solvent. An aromatic concentrate, containing water and being substantially free of solvent and non-aromatics, is withdrawn as an overhead vapor stream from SRC 332 and introduced into an overhead receiver D2 352 via line 51 after being condensed in a cooler (not shown). In order to minimize the bottom temperature in SRC 332, receiver D2 352 is connected to a vacuum source to generate sub-atmospheric conditions in SRC 332.

Overhead receiver D2 352 serves to effect a phase separation between the aromatic HC and the water phases. A portion of the aromatic HC phase in line 52 is recycled to the top of SRC 332 as reflux via line 53, while the remainder portion is withdrawn as aromatic HC product through line 54. A portion of the lean solvent from the bottom of SRC 332 is heated in the reboiler R2 354 and recycled to the bottom of SRC 332 via line 57. The majority of the lean solvent exiting from the bottom of SRC 332 is transferred into EDC 330 via lines 56, 58, and 61.

The water phase that accumulates in the water leg of overhead receiver D2 352 is fed via line 55 to WWC 344 as wash water at a location below the interface between the HC and the water phases near the top of WWC 344. Solvent is removed from the HC phase from SCC 340 through a counter-current water wash and the solvent-free non-aromatics, which accumulate in the HC phase, are withdrawn from the top of WWC 344 as a product through lines 69 and 70. A water phase, containing the solvent, exits through lines 62 and 67 from the bottom of WWC 344 and is combined with line 48 that is the water phase from overhead receiver D1 346 and is fed to steam generator SR1 342 via line 63 where it is transformed into stripping stem that is introduced into SRC 332 via line 64.

A split stream 59 of the lean solvent from SRC 332 in line 58 containing a measurable amount of heavy HCs is cooled in the cooler C1 348. After being cooling, a slip water-rich stream from the bottom of WWC 344 is then added via lines 62 and 68 to the stream 59 to form stream 60 to provide a controlled amount of water to the lean solvent stream as the co-displacement agent. This lean solvent stream with increased water content is introduced via line 60 into the upper portion of SCC 340 below the location of the solvent/HC interface.

A portion of the raffinate stream from EDC 330 is fed to SCC 340 via line 49 to contact the solvent phase as the displacement agent to squeeze out the heavy HCs and PMs from the solvent phase into the HC phase in SCC 340. A solvent phase, that contains essentially purified solvent, most of the aromatic components from the raffinate stream (the displacement agents), and substantially reduced levels of heavy HCs and PMs, is continuously withdrawn from lower portion of SCC 340 and introduced through line 65 to the lower portion of EDC 330 where the single liquid phase region exists. This is the way to recycle the purified solvent into the solvent loop, to recover the aromatic HCs, especially benzene, which is lost to the raffinate stream, and to improve the solvent selectivity in the single liquid phase region of EDC 330 due to higher water content in the solvent.

The HC phase accumulating continuously at the top of SCC 340 is removed periodically from the overhead of SCC 340 and fed to WWC 344 via line 66, where any solvent in the final raffinate product is removed.

In an application of the ED process of FIG. 2 using sulfolane as the solvent, the EDC is operated at a reduced solvent-to-HC feed weight ratio of 2.0 to 4.0, preferably 1.5 to 3.0, depending upon the boiling range of the HC feedstock, to allow 1 to 10 wt %, preferably 2 to 5 wt % benzene the raffinate stream from the EDC overhead. Preferably, the portion of the lean solvent that withdrawn from the bottom of SRC 332 and directed to cooler C1 348 is cooled to a temperature typically in the range of approximately 0 to 100° C., and preferably of 25 to 80° C. Temperature of the raffinate stream fed to SCC 340 as the displacement agent ranges from 0 to 100° C., preferably from 25 to 50° C. In addition, raffinate feed-to-solvent feed weight ratio in SCC 340 typically ranges from 0.1 to 100, and preferably from 0.1 to 10. The contacting temperature in SCC 340 typically ruins 0 to 100° C. and preferably from 25 to 80° C. The operating pressure of SCC 340 typically is from 1 to 100 atm., and preferably from 1 to 10 atm. The weight ratio between the cooled solvent-rich stream mixture in line 59 and the water-rich stream in line 68 is in the range of 200:1 to 10:1 preferably in the range of 100:1 to 20:1, by adjusting the flow rate of the water-rich stream in line 68. Again, operation condition of SCC 340 is selected to achieve the objectives outlined for the process of FIG. 1.

FIG. 3 is a LLE process for aromatic HC recovery, employing liquid-liquid extraction (LLE) column 400, solvent recovery column (SRC) 402, solvent regenerator (SRG) 404, solvent clean-up column (SCC) 406, water washing column (WCC) 408, extractive stripper column (ESC) 410 and inline magnetic filter (MF) 412. A HC feed containing aromatics and non-aromatics is fed via line 102 to the middle portion of LLE column 400, while lean solvent is introduced near the top of LLE column 400 via line 103 to counter-currently contact the HC feed. The aromatic HCs in the feed typically comprise benzene, toluene, ethylbenzene, xylenes, $C_9^+$ aromatics, and mixtures thereof, and the non-aromatic hydrocarbons typical comprise $C_5$ to $C_9^+$ paraffins, naphthenes, olefins, and mixtures thereof.

A raffinate phase containing essentially the non-aromatics with minor amounts of solvent is withdrawn from the top of LLE column 400 as stream 104 and is fed to a middle portion of WWC 408 via line 132 after combining stream in line 130. An extract phase from the bottom of LLE column 400 in line 105 is mixed with a secondary lean solvent from line 106; the combined stream 107 is fed to the top of ESC 410.

The vapor flow through ESC 410 is generated by the action of reboiler R1 414, whereby a portion of the rich solvent in the bottom is recycled to ESC 410 via line 111 through reboiler R1 414 which is normally heated by steam at a rate that is sufficient to control the column bottom temperature, the overhead stream composition and the flow rate. Overhead vapor exiting the top of ESC 410 is condensed in a cooler (not shown) and the condensate is transferred via line 108 to an overhead receiver D1 416, which serves to effect a phase separation between the HC and the water phases. The HC phase, containing the non-aromatics and up to 30-40% benzene and heavier aromatics, is recycled to the lower portion of LEE column 400 as reflux via line 109. The water phase is transferred via lines 110 and 125 to steam generator SR1 418 to generate stripping steam for SRC 402. A rich solvent consisting of the solvent, aromatics free of non-aromatics, and measurable amounts of heavy HCs and PMs is withdrawn from the bottom of ESC 410 and transferred to the middle portion of SRC 402 via line 112. Stripping steam is injected from steam generator SR1 418 via line 126 into the lower portion of SRC 402 to assist in the removal of aromatic HCs from the solvent. An aromatic concentrate, containing water and being substantially free of solvent and non-aromatic HCs, is withdrawn as an overhead vapor stream from SRC 402 and introduced into an overhead receiver D2 420 via line 113 after being condensed in a cooler (not shown). In order to minimize the bottom temperature of SRC 402, overhead receiver D2 420 is connected to a vacuum source to generate sub-atmospheric conditions in SRC 402.

Overhead receiver D2 420 serves to effect a phase separation between the aromatic HC and the water phases. A portion of the aromatic HC phase in line 114 is recycled to the top of SRC 402 as reflux via line 115, while the remainder portion is withdrawn as aromatic HC product through line 116. The water phase that accumulates in the water leg of overhead receiver D2 420 is fed via line 136 to WWC 408 as wash water at a location below the interface between the HC phase and the water phase near the top of WWC 408. The solvent is removed from the LLE raffinate and the HC phase from SCC 406 through a counter-current water wash and the solvent-free non-aromatics, which accumulate in the HC phase, are then withdrawn from the top of WWC 408 as solvent-free non-aromatic products through line 137. A water phase, containing the solvent, exits through lines 133 and 134 from the bottom of WWC 408 and is combined with line 110, that is the water phase from overhead receiver D1 416, and is fed to steam generator SR1 418 via line 125 where it is transformed into stripping steam that is introduced into SRC 402 via line 126 and into SRG 404 via line 122.

A greater proportion of the lean solvent from the bottom of SRC 402 is recycled through a magnetic enhanced filter MF 412 via lines 118, 120, 121 and 103 and is supplied to the upper portion of LLE column 400 for extracting the aromatic HCs in LLE column 400. A split stream of the lean solvent from the SRC bottom is diverted into SRG 404 via line 119 and steam is introduced into SRG 404 through line 122, at a location below the lean solvent feed entry point. A portion of the lean solvent is heated in reboiler R2 422 and recycled to the bottom of SRC 402 via line 117. Deteriorated solvent and polymeric sludge are removed as a bottom stream through line 124, while the regenerated solvent and substantially all the stripping steam, are recovered as an overhead stream 123. This vapor in line 123 and a split lean solvent from the bottom of SRC 402 in line 127 are combined to form the mixture in line 128, which contains the solvent, a measurable amount of heavy HCs and substantially all the stripping steam from SRG 404. In operation, after the vapor is cooled and condensed in cooler C1 424, a slip water-rich stream from the bottom of WWC 408 is added to the stream in line 128 to provide a controlled amount of water via line 135 to the lean solvent stream as a co-displacement agent. The mixture is then introduced into the upper portion of SCC 406 below the location of solvent/HC interface.

A portion of the raffinate stream from the LLE column is fed to the lower portion of SCC 406 via line 129 as the displacement agent to contact the solvent phase counter-currently to squeeze out the heavy HCs and PMs from the solvent phase into the HC phase in SCC 406. Alternatively, a external desulfurized light HC stream can be used effectively as the displacement agent. A solvent phase containing essentially purified solvent, most of the aromatics components from the raffinate stream (the displacement agent), and substantially reduced levels of heavy HCs and PMs is continuously withdrawn from the bottom of SCC 406 and introduced through line 131 into the lower portion of ESC 410, to recycle the purified solvent into the solvent loop, to enhance the solvent selectivity in the single phase region of the ESC due to increased water content (the co-displacement agent) in the recycled solvent phase from SCC 406.

The HC phase that accumulates continuously at the top of SCC 406 is removed periodically from the overhead of SCC 406 via lines 130 under interface level control, which is then mixed with the raffinate stream from the overhead of LLE column 400 and fed via line 132 to WWC 408. The solvent clean-up operation may also be conducted in any other continuous multi-stage contacting device, preferably one that is designed for counter-current extraction, such as multi-stage mixers/settlers, or any other rotating type contactors.

In an application of the LLE process of FIG. 3 using sulfolane as the solvent, the temperature of the overhead vapor from SRG 404 typically ranges from 150° to 200° C. and preferably from 160° to 180° C., under a pressure of 0.1 to 10 atm., and preferably of 0.1 to 0.8 atm. The mixture comprising of solvent vapor from SRG 404 and lean solvent from SRC 402 is condensed and cooled in the cooler C1 424 to a temperature in the range of approximately 0 to 100° C., and preferably of 25 to 80° C. The temperature of the raffinate stream from LLE column 400, which is fed to SCC 406 as the displacement agent, ranges from 0 to 100° C., preferably from 25 to 50° C. The raffinate feed-to-lean solvent feed weight ratio in SCC 406 is typically from 0.1 to 100, and preferably from 0.1 to 10. The contacting temperature in SCC 406 typically ranges from 0° to 100° C. and preferably from 25 to 80° C. The operating pressure of SCC 406 typically ranges from 1 to 100 atm., and preferably from 1 to 10 atm. The weight ratio between the cooled solvent-rich stream mixture in line 128 and the water-rich stream in line 135 is in the range of 200:1 to 10:1, preferably in the range of 100:1 to 20:1 and is achieved by adjusting the flow rate of the water-rich stream in line 135. The operational requirements of SCC 406 are the same as for SCC 310 and SCC 340 for the schemes of FIGS. 1 and 2, respectively.

FIG. 4 illustrates a LLE process for aromatic HCs recovery from the mixture containing aromatic HCs and non-aromatic HCs, in which a solvent clean-up column (SCC) 436 uses the raffinate from LLE column 430 as the displacement agent to regenerate the lean solvent. A high temperature and energy intensive conventional thermal regenerator is not required.

The process employs liquid-liquid extraction (LLE) column 430, solvent recovery column (SRC) 432, solvent clean-up column (SCC) 436, water washing column (WWC) 438, extractive stripper column (ESC) 440, and inline magnetic filter enhanced with magnetic field (MF) 442. A HC feed containing aromatic and non-aromatics is fed via line 202 to the middle portion of LLE column 430, while lean solvent is introduced near the top of LLE column 430 via line 203 to counter-currently contact the HC feed. A raffinate phase in stream 204 containing essentially the non-aromatics with minor amounts of solvent is withdrawn from the top of LLE column 430 and is fed to a middle portion of WWC 438 via line 227 after combining the stream in line 226. An extract phase is transferred from the bottom of LLE column 430 via line 205 and is mixed with a secondary lean solvent from line 206; the combined stream 207 is fed to the top of ESC 440.

The vapor flow through ESC 440 is generated by the action of reboiler R1 444, whereby a portion of the rich solvent in bottom is recycled to ESC 440 via line 211 through reboiler R1 444 which is normally heated by steam at a rate that is sufficient to control the column bottom temperature, the overhead stream composition and the flow rate. Overhead vapor exiting the top of ESC 440 is condensed in a cooler and the condensate is transferred via line 208 to an overhead receiver D1 446, which serves to effect a phase separation between the HC and the water phases. The HC phase, containing the non-aromatics and up to 30-40% benzene and heavier aromatics, is recycled to the lower portion of LLE column 430 as reflux via line 209. The water phase is transferred via lines 210 and 221 to steam generator SR1 448 to generate stripping steam for SRC 432. A rich solvent consisting of the solvent, purified aromatics and measurable amounts of heavy HCs and PMs is withdrawn from the bottom of ESC 440 and transferred to the middle portion of SRC 432 via line 212. Stripping steam is injected from steam generator SR1 448 via line 222 into the lower portion of SRC 432 to assist in the removal of aromatic HCs from the solvent. An aromatic concentrate, containing water and being substantially free of solvent and non-aromatics, is withdrawn as an overhead vapor stream from SRC 432 and introduced into an overhead receiver D2 450 via line 213 after being condensed in a cooler. In order to minimize the bottom temperature of SRC 432, overhead receiver D2 450 is connected to a vacuum source to generate sub-atmospheric conditions in SRC 432.

Overhead receiver D2 450 serves to effect a phase separation between the aromatic HC and the water phases. A portion of the aromatic HC phase in line 214 is recycled to the top of SRC 432 as reflux via line 215, while the remainder portion is withdrawn as aromatic HC product through line 216. A portion of the lean solvent from the bottom of the SRC 432 is heated in the reboiler R2 452 and recycled to the bottom of SRC 432 via line 217. Preferably, the majority of the lean solvent exiting from the bottom of SRC 432 is transferred into LLE column 430 via lines 218, 220, and 203.

The water phase that accumulates in the water leg of overhead receiver D2 450 is fed via line 231 to WWC 438 as wash water at a location below the interface between the HC and the water phases near the top of WWC 438. Solvent is removed from the LLE raffinate through a counter-current water wash and the solvent-free non-aromatics, which accumulate in the HC phase, are withdrawn from the top of WWC 438 as a product through line 232. A water phase, containing the solvent, exits through lines 228 and 229 from the bottom of WWC 438 and is combined with line 210 that is the water phase from overhead receiver D1 446 and is fed to steam generator SR1 448 via line 221 where it is transformed into stripping steam that is introduced into SRC 432 via line 222.

A split stream 219 of the lean solvent from SRC 432 in line 218 which contains measurable amounts of heavy HCs is cooled in cooler C1 454. A slip water-rich stream from the bottom of WWC 438 is then added via line 230 to stream 219 to form stream 223 which provides a controlled amount of water to the lean solvent stream as the a co-displacement agent. This lean solvent stream with enhanced water content is introduced via line 223 into the upper portion of SCC 436 below the location of the solvent/HC interface.

A portion of the raffinate stream from LLE column 430 contacts the solvent phase as the displacement agent to squeeze out the heavy HCs and PMs from the solvent phase into the HC phase in the SCC. A solvent phase, that contains essentially purified solvent, most of the aromatic components from the raffinate stream (the displacement agents), and substantially reduced levels of heavy HCs and PMs, is continuously withdrawn from lower portion of SCC 436 and introduced through line 225 to the lower portion of ESC 440 where the single liquid phase region exists. This recycles the purified solvent into the solvent loop and to improve the solvent selectivity in the single liquid phase region of ESC 440 due to higher water content in the solvent. A filter MF 442 that is enhanced with a magnetic field is positioned in the main lean recycle line between SRC 432 and LLE column 430.

The HC phase which accumulates continuously at the top of SCC 436 and is removed periodically from the overhead of SCC 436 via line 226 under interface level control, which is then mixed with the raffinate stream from the overhead of LLE column 430 before being fed via line 227 to WWC 438 where any solvent in the final raffinate product is removed.

In an application of the LLE process that is depicted in FIG. 4 with sulfolane as the solvent, the portion of the lean solvent that withdrawn from the bottom of SRC 432 and directed to cooler C1 454 is cooled to as temperature typically in the range of approximately 0 to 100° C., and preferably of 25 to 80° C. Temperature of the raffinate stream fed to SCC 436 as the displacement agent ranges from 0 to 100° C., preferably from 25 to 50° C. In addition, raffinate feed-to-solvent feed weight ratio in SCC 436 typically ranges from 0.1 to 100, and preferably from 0.1 to 10. The contacting temperature in the SCC typically ranges from 1 to 100° C., and preferably from 25 to 80° C. The operating pressure of SCC 436 typically is from 1 to 100 atm., and preferably from 1 to 10 atm. The weight ratio between the cooled solvent-rich stream mixture in line 219 and the water-rich stream in line 230 is in the range of 200:1 to 10:1, preferably in the range of 100:1 to 20:1, by adjusting the flow rate of the water-rich stream in line 230. Operation conditions of SCC 436 are selected to achieve the objectives outlined in the process of FIG. 1.

What is claimed is:

1. A method for recovering a polar hydrocarbon (HC) selective solvent substantially free of hydrocarbon (HC) impurities from a solvent-rich stream containing the selective solvent, measurable amounts of heavy HCs, and polymeric materials (PMs) generated from reactions among thermally decomposed or oxidized solvent, heavy HCs, and additives, which method comprises the steps of:

(a) introducing a feed containing polar and less polar HCs into a middle portion of an extractive distillation column (EDC) and introducing a solvent-rich stream into an upper portion of the EDC as a selective solvent feed;

(b) recovering a water-containing, less polar HC-rich stream from a top of the EDC and withdrawing a first solvent-rich stream containing solvent and polar HCs from a bottom of the EDC;

(c) introducing the first solvent-rich stream into a middle portion of a solvent recovery column (SRC), recovering a polar HC-rich stream, that is substantially free of solvent and less polar HCs, from a top of the SRC, and removing a second solvent-rich stream from a bottom of the SRC;

(d) introducing a first portion of the second solvent-rich stream into the upper portion of the EDC in step (a) as the selective solvent feed;

(e) cooling a second portion of the second solvent-rich stream in step (c), mixing the cooled solvent-rich stream with a portion of water phase from step (h), and introducing the mixture into an upper portion of a solvent clean-up zone to form a solvent phase;

(f) introducing a light HC-rich stream into a lower portion of the solvent clean-up zone, as a heavy HC displacement agent, to squeeze out heavy HCs and PMs from the solvent phase into a HC phase;

(g) withdrawing an accumulated HC phase containing heavy HCs, PMs and minor amounts of solvent from an upper portion of the solvent clean-up zone, and recovering a solvent phase containing solvent and light HCs, which serves as heavy HC displacement agents, and has substantially reduced levels of heavy HCs and PMs, from a lower portion of the solvent clean-up zone;

(h) introducing the HC phase from the solvent clean-up zone in step (g) into a water wash zone to remove the minor amounts of solvent from the HC phase into the water phase; and (i) introducing the solvent phase from the solvent clean-up zone in step (g) into a lower portion of the EDC in step (a) as part of a selective solvent feed to recycle purified solvent into a solvent loop.

2. The method of claim 1 wherein in step (c) the second solvent-rich stream is filtered through an in-line filter that is enhanced with a magnetic field before entering the upper portion of the EDC and the solvent cleanup zone.

3. The method of claim 1 wherein step (d) comprises introducing a greater portion of the second solvent-rich stream into an upper portion of the EDC and introducing a first minor portion of the second solvent-rich stream into an upper portion of a thermal solvent regeneration zone, recovering a third solvent-rich stream containing solvent, water, and HCs and other compounds having boiling points below that of the solvent, from a top of the solvent regeneration zone, and removing heavy sludge from a lower portion of the solvent regeneration zone and wherein step (e) comprises cooling a mixture that comprises the third solvent-rich stream in step (d) and a second minor portion of the second solvent-rich stream in step (c), combining the cooled solvent-rich mixture with a portion of the water phase from step (h), and introducing the mixture into an upper portion of a solvent cleanup zone to form the solvent phase.

4. The method of claim 1 wherein the polar HCs are aromatic and said less polar HCs are paraffinic, naphthenic, and olefinic.

5. The method of claim 1 wherein the solvent is selected from a group consisting of sulfolane, alkyl-sulfolane, N-formyl morpholine, N-methylpyrrolidone, tetraethylene glycol, triethylene glycol, diethylene glycol, and mixtures thereof, with water as a co-solvent.

6. The method of claim 1 wherein the solvent is sulfolane with water as a co-solvent.

7. The method of claim 1 wherein the solvent is N-formyl morpholine.

8. The method of claim 1 wherein the light HC-rich stream is the less polar HC-rich stream from overhead of the EDC.

9. The method of claim 1 wherein the light HC-rich stream is an external benzene-free stream containing $C_5$-$C_8$ hydrocarbons.

10. The method of claim 1 wherein the EDC is operated under conditions as to allow 1 to 10 wt % benzene in a water-containing, less polar HC-rich stream from a top of the EDC by keeping substantially all $C_9$, HCs in the first solvent-rich stream.

11. The method of claim 1 wherein the EDC is operated under conditions as to allow 2 to 5 wt % benzene in a water-containing, less polar HC-rich stream from a top of the EDC by keeping substantially all $C_9$, HCs in the first solvent-rich stream.

12. The method of claim 1 wherein the SRC is operated under conditions as to strip only $C_8$ and lighter hydrocarbons from the first solvent-rich stream and to keep substantially all $C_9$ and heavier hydrocarbons in the second solvent-rich stream.

13. The method of claim 1 wherein in step (e) the weight ratio between the cooled solvent-rich stream and the water phase is in a range of 200:1 to 10:1.

14. The method of claim 1 wherein in step (e) the weight ratio between the cooled solvent-rich stream and the water phase is in a range of 100:1 to 20:1.

15. A method for recovering a polar hydrocarbon (HC) selective solvent substantially free of hydrocarbon (HC) impurities from a solvent-rich stream containing the selective solvent, measurable amounts of heavy HCs, and polymeric materials (PMs) generated from reactions among thermally decomposed or oxidized solvent, heavy HCs, and additives, which method comprises the steps of:

(a) introducing a feed containing polar and less polar HCs into a middle portion of a liquid-liquid extraction column (LLE) and introducing a solvent-rich stream into an upper portion of the LLE as a selective solvent feed;

(b) recovering a water-containing, less polar HC-rich stream from a top of the LLE and withdrawing the first solvent-rich stream containing solvent, polar HCs and minor amounts of less polar HCs from a bottom of the LLE;

(c) introducing a mixture comprising the first solvent-rich stream and a minor portion of a third solvent-rich stream from a bottom of a solvent recovery column (SRC), into an upper portion of an extractive stripping column (ESC), recovering a HC-rich vapor containing less polar HCs and benzene and heavier aromatics, which is condensed and recycled to a lower portion of LLE as a reflux, and withdrawing a second solvent-rich stream containing solvent and polar HCs, which is substantially free of less polar HCs, from a bottom of the ESC;

(d) introducing the second solvent-rich stream in step (c) into a middle portion of the SRC, withdrawing a polar HC-rich stream, which is substantially free of solvent and non-polar HCs, from a top of the SRC, and removing a third solvent-rich stream from a bottom of the SRC;

(e) introducing a portion of the third solvent-rich stream into the upper portion of the LLE in step (a) as the selective solvent feed;

(f) cooling a minor portion of the third solvent-rich stream in step (d), mixing the cooled solvent-rich stream with a portion of water phase from step (i), and introducing the mixture into an upper portion of a solvent clean-up zone to form a solvent phase;

(g) introducing a light HC-rich stream into a lower portion of the solvent clean-up zone, as a heavy HC displacement agent, to squeeze out heavy HCs and PMs from the solvent phase into a HC phase;

(h) withdrawing an accumulated HC phase containing heavy HCs, PMs, and minor amounts of solvent from an upper portion of the solvent cleanup zone and recovering the solvent phase containing solvent, light HCs, which serves as heavy hydrocarbon displacement agents, and having substantially reduced levels of heavy HCs and PMs, from a lower portion of the solvent clean-up zone;

(i) introducing the HC phase from the solvent cleanup zone in step (h) into a water wash zone to remove the minor amounts of solvent from the HC phase into the water phase;

(j) introducing the solvent phase from the solvent clean-up zone in step (h) into a lower portion of the ESC in step (c) to recycle purified solvent into a solvent loop.

16. The method of claim 15 wherein in step (e) the third solvent-rich stream is filtered through an in-line filter that is enhanced with a magnetic field before entering the upper portion of the LLE.

17. The method of claim 15 wherein step (e) comprises introducing a greater portion of the third solvent-rich stream into the upper portion of the LLE in step (a) and introducing a first minor portion of the third solvent-rich stream into an upper portion of a high-temperature thermal solvent regeneration zone, recovering a fourth solvent-rich stream containing solvent, water, and HCs having boiling points below that of the solvent, from a top of the solvent regeneration zone, and removing heavy sludge from a lower portion of the solvent regeneration zone and wherein step (f) comprises cooling a mixture that comprises the third solvent-rich stream in step (e) and a second minor portion of the third solvent-rich stream in step (d), combining the cooled solvent-rich mixture with a portion of water phase from step (i), and introducing the mixture into an upper portion of a solvent cleanup zone to form a solvent phase.

18. The method of claim 15 wherein the polar hydrocarbons are aromatic and said less polar hydrocarbons are paraffinic, naphthenic, and olefinic.

19. The method of claim 15 wherein the solvent is selected from a group consisting of sulfolane, alkyl-sulfolane, N-formyl morpholine, N-methylpyrrolidone, tetraethylene glycol, triethylene glycol, diethylene glycol, and mixtures thereof, with water as a co-solvent.

20. The method of claim 15 wherein the solvent is sulfolane with water as a co-solvent.

21. The method of claim 15 wherein the solvent is tetraethylene glycol with water as a co-solvent.

22. The method of claim 15 wherein the light HC-rich stream is the less polar HC-rich stream from overhead of the LLE column.

23. The method of claim 15 wherein the light HC-rich stream is an external benzene-free stream containing $C_5$-$C_8$ hydrocarbons.

24. The method of claim 15 wherein in step (f) the weight ratio between the cooled solvent-rich stream and the water phase is in a range of 200:1 to 10:1.

25. The method of claim 15 wherein in step (f) the weight ratio between the cooled solvent-rich stream and the water phase is in a range of 100:1 to 20:1.

* * * * *